United States Patent
Abri

(10) Patent No.: US 10,114,928 B2
(45) Date of Patent: Oct. 30, 2018

(54) METHOD AND DEVICE FOR DOCUMENTING MEDICAL DATA

(75) Inventor: Omid Abri, Berlin (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 1526 days.

(21) Appl. No.: 12/270,462

(22) Filed: Nov. 13, 2008

(65) Prior Publication Data

US 2009/0144090 A1    Jun. 4, 2009

Related U.S. Application Data

(60) Provisional application No. 60/987,610, filed on Nov. 13, 2007.

(30) Foreign Application Priority Data

Nov. 13, 2007  (EP) ..................................... 07022002

(51) Int. Cl.
  *G06Q 50/22*     (2018.01)
  *G06F 19/00*     (2018.01)
  (Continued)

(52) U.S. Cl.
  CPC .......... *G06F 19/3418* (2013.01); *G06F 19/00* (2013.01); *G06Q 50/22* (2013.01); *G06Q 50/24* (2013.01); *G16H 40/20* (2018.01)

(58) Field of Classification Search
  CPC ..... G06F 19/00; G06F 19/3418; G06Q 50/22; G06Q 50/24; G16H 40/20
  (Continued)

(56) References Cited

U.S. PATENT DOCUMENTS 5,605,531 A *  2/1997  Lane ...................... A61B 1/042
                                                     348/74
5,654,750 A *  8/1997  Weil ...................... G09B 5/065
                                                    348/143

(Continued)

FOREIGN PATENT DOCUMENTS

DE         19904090 A1    8/2000
DE     102005025903 A1   12/2006
(Continued)

OTHER PUBLICATIONS

Guerlain S. et al: "Assessing team performance in the operating room: Development and use of a "black-box" recorder and other tools for the intraoperative environment" Journal of The American College of Surgeons, College, Chicago, IL, US, Bd. 200, Nr. 1, Jan. 1, 2005 (Jan. 1, 2005), Seiten 29-37.

(Continued)

*Primary Examiner* — Hiep V Nguyen
(74) *Attorney, Agent, or Firm* — Whitmyer IP Group LLC

(57) ABSTRACT

A method for documenting medical data in which the data captured by at least one data entry device from an operating room are stored in a storage medium wherein storage is activated only by the presence in the operating room of a patient who is to be operated on. A device for documenting medical data includes at least one data reception device for entering data from at least one data source, at least one visual display unit for showing data for a user, and at least one entry device for entering data and/or instructions by the user, wherein the storage device includes a data memory that is configured for automatic erasing and/or overwriting of stored data after a predetermined period.

20 Claims, 2 Drawing Sheets

(51) Int. Cl.
  *G06Q 50/24* (2012.01)
  *G16H 40/20* (2018.01)
(58) Field of Classification Search
  USPC .............................................................. 705/3
  See application file for complete search history.

(56) References Cited

U.S. PATENT DOCUMENTS

| | | | |
|---|---|---|---|
| 6,304,948 B1 * | 10/2001 | Motoyama | G06F 21/80 711/144 |
| 6,955,671 B2 * | 10/2005 | Uchikubo | 600/118 |
| 7,231,135 B2 | 6/2007 | Esenyan et al. | |
| 7,494,464 B2 * | 2/2009 | Rzesnitzek | A61B 5/1115 128/920 |
| 7,667,606 B2 * | 2/2010 | Packert et al. | 340/573.1 |
| 2003/0108327 A1 | 6/2003 | Sunagawa | |
| 2003/0159141 A1 | 8/2003 | Zacharias | |
| 2005/0203350 A1 * | 9/2005 | Beck | 600/300 |
| 2005/0283047 A1 * | 12/2005 | Tashiro et al. | 600/118 |
| 2007/0294105 A1 * | 12/2007 | Pierce | G06F 19/321 705/2 |
| 2009/0204434 A1 * | 8/2009 | Breazeale, Jr. | 705/3 |

FOREIGN PATENT DOCUMENTS

| | | |
|---|---|---|
| EP | 1034480 B1 | 12/2005 |
| FR | 2856222 A1 | 12/2004 |
| WO | 0057336 A1 | 9/2000 |
| WO | 0219957 A2 | 3/2002 |
| WO | 2007073420 A1 | 6/2007 |

OTHER PUBLICATIONS

European Search Report; EP 08 01 9805; dated Dec. 23, 2008; 3 pages.
European Search Report; EP 07 02 2002; dated Jun. 12, 2008; 4 pages.

\* cited by examiner

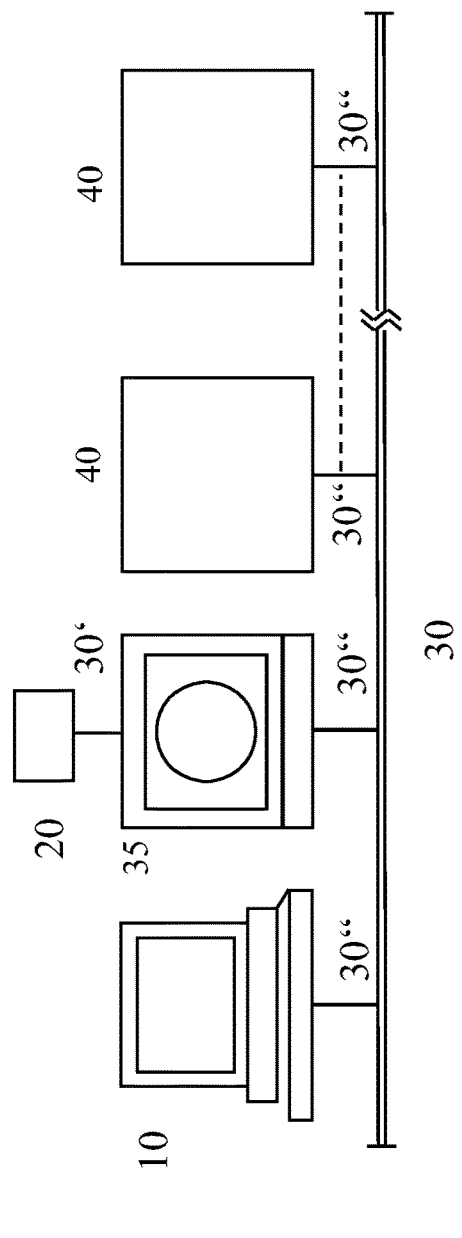

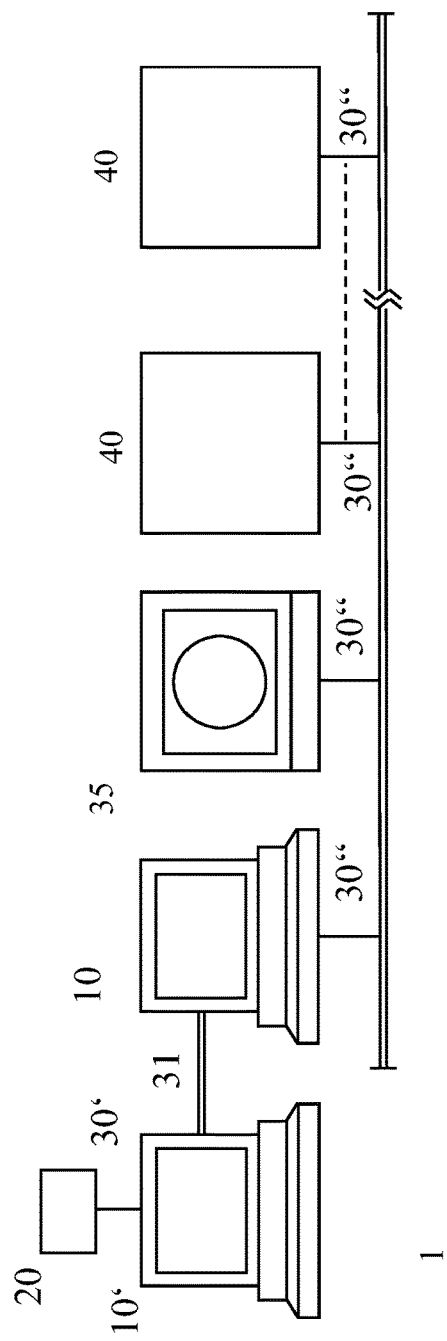
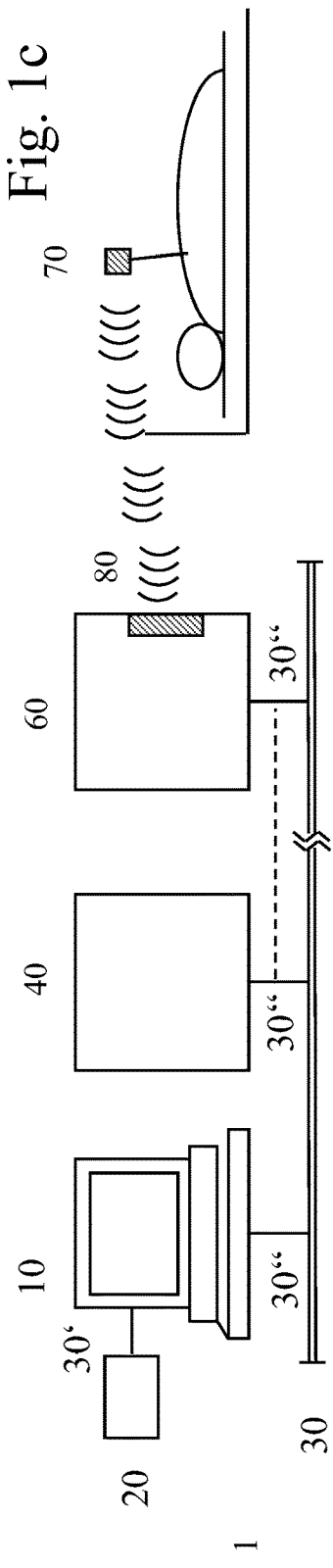

METHOD AND DEVICE FOR DOCUMENTING MEDICAL DATA

CROSS-REFERENCE TO RELATED APPLICATIONS

The present application claims priority of European patent application No. 07 022 002.5 filed on Nov. 13, 2007. The present application also claims the benefit under 35 U.S.C. § 119 (e) of the U.S. Provisional Patent Application Ser. No. 60/987,610, filed on Nov. 13, 2007. All prior applications are herein incorporated by reference in their entirety.

FIELD OF THE INVENTION

The present invention relates to a method as well as a device for documenting medical data.

Methods and devices of this type are known in the art. For instance, there are known endoscopic image documentation systems with which certain image data together with corresponding patient information can be entered, processed, and stored. One example of such a system is offered in various models under the name KARL STORZ AIDA®.

Such an image documentation system can be connected with a central bus-supported OR control by means of an interface. Such an OR control and such a bus system are disclosed for instance in EP 1 034 480 B1 and in WO 02/19957 A2. It is also known in the art to use such a data logger for recording intraoperative devices or functional parameters on a central memory unit.

Moreover, WO 2007/073420 A1, DE 10 2005 025 903 A1, and U.S. Pat. No. 7,231,135 B2 teach systems for storing and processing medical data, in particular medical video data.

If all the known systems for documenting medical data led to a continuous registration, in particular a continuous video recording, of all activities in the operating room (OR), then in a relatively short time the storage media would be overrun and no further storage could take place. On the other hand, for purposes of retrospective quality control in the OR, it is desirable to be able to resort to a complete video record.

The non-related disclosure US 2003/0108327 A1 teaches an image recording system in which image data are stored in a cyclical storage device and regularly overwritten. After an alarm signal is generated, a new storage of image data occurs with unmodified image frequency, but previously stored image data remain on the storage medium with reduced image frequency.

U.S. Pat. No. 5,654,750 discloses an automatic recording and storage system for a hospital. Video data are transcribed outside the hospital and stored on storage devices, in particular video recorders. The system can include several video recorders for an uninterrupted, overlapping storage of all recordings if there is a regular exchange of video tapes as required. To economize on storage space, the video recorders are started automatically or started up again if movement or light in the OR is registered or no longer registered by motion sensors and photoelectric sensors situated in the OR. This requires, however, frequent and complex exchange of video tapes. Another disadvantage is that the storage is activated independently of the type of activity in the OR, for instance also during cleaning or maintenance tasks or else when person pass through an OR. This causes recordings that are not relevant for archiving or quality control and use up storage space unnecessarily and cause unnecessary expense in issuing and evaluating a relevant recording.

It is the object of the present invention to provide a method and device with which continuous storage of medical data, in particular video data and/or speech data from an OR, is possible, and where the storage of non-relevant data is largely avoided.

SUMMARY OF THE INVENTION

This object is met by means of a method for documentation of medical data, a device for documenting medical data, and a system for conducting medical interventions.

According to the invention, the data to be documented are captured by at least one data entry device. This data entry device is, in particular, positioned in an operating room and can, for instance, take the form of a video camera that takes in the entire operating room or a portion of it. Alternatively, the data entry device can capture data of other types from the OR, such as sound or speech, or else data relating to surgical or other types of devices found in the OR or data that are produced by these devices. The captured data can, in particular, be incorporated in real time into a storage device and can be stored on a storage medium. To avoid storage of non-relevant data and thus any unnecessary storage and evaluation expense, the storage action is dependent on the presence of a patient in the operating room. In particular, storage is activated when the patient who is to be operated on is brought into the operating room. The patient's presence in the OR can be recognized in this case by sensors that are sensitive to attributes associated with the patient, so that the recording is started or turned off again automatically. A range of sensor systems can be used for this purpose, for instance a video camera leading to an automatic image analysis.

In preferred manner, storage is deactivated when the patient leaves the OR. In this case the patient's presence in the OR can be recognized directly or the patient's entrance into the OR or the patient's departure from the OR in an entry or departure area of the OR.

In this manner the object of the invention is fully realized.

According to a preferred embodiment of the inventive method, storage is activated only by the presence of an additional predetermined person in the operating room, said person being present in the OR in addition to the patient. The additional person here can in particular be a physician or anesthesiologist or a surgeon, in particular one assigned to perform the particular operation or responsible for it. The presence of the additional person can, in particular, be recognized in the same manner as that of the patient. The start and/or end of the data recording can also be dependent on the simultaneous presence of several additional predetermined persons, in particular on the simultaneous presence of surgeon and anesthesiologist. Likewise, the storage can be made dependent on the presence of one or more persons in a predefined group, when for instance a substitution for the operating surgeon, or an alternation with that person, is intended.

In this manner, storage is activated only when the surgical intervention is taking place, and not during a possible preparatory or waiting period. This arrangement makes it possible to avoid otherwise unnecessary storage or evaluation expenditure, so that those data are stored that are necessary for quality assurance, for documentation, or else for the performance of the operation in the event of later occurrence of complications.

According to another embodiment of the inventive method, the data are at least partially captured by a network, a computer system, and/or a medical device, in particular an endoscopic video camera. Such a network could be a bus-supported network that is installed in the OR for control of all operation-associated functions and that can also be connected with an over-arching network, such as a hospital information system (HIS) and/or an OR management or planning system. Patient data, for instance, can also be captured and stored by means of such a network. Data on the criteria for starting and/or ending storage, such as the identification of the patient or of additional persons, can also be captured for instance by such a network.

As a result, the availability of all relevant data is insured in a simple manner. In addition, storage can take place at a site separate from the OR.

In preferred manner the data include image information, in particular endoscopic image information. Such image information is produced during video-supported endoscopic operations and thus are automatically made available for storage. This image information, in particular, is particularly relevant for quality assurance, documentation, and possibly for the subsequent ascertainment of causes of possible complications. Likewise it is possible to store image data captured by a room video camera and/or speech data, for instance speech and noises captured by a microphone in the OR or commands captured by a speech control. This ensures storage of all possibly relevant data.

In especially preferred manner, the data include information on the type and/or location and/or function and/or parameters of surgical instruments and/or devices. Such surgical instruments or appliances are, for instance, endoscopic instruments, endoscope lens systems, insufflators, HF generators, and so on. It can be important for documentation purposes it can be important to store the type of instruments or appliances used and also, for instance, the serial numbers. Devices used in the OR also often have a function control, which supplies data for instance on the pressure and flow of an insufflation gas. If the devices are integrated in a network installed in the OR, then data on the type, function, and entered parameters of the devices are automatically available for storage; also additional devices, such as room illumination or an automated OR table, can be included here. The location of the instruments or appliances in the OR can also be captured by an automatic, possibly wireless system. It is also possible to ensure storage of manually entered data on the type, location, function, and/or parameters of the instruments or appliances used.

Consequently, a particularly complete storage of all possibly relevant data is ensured.

According to an additional embodiment of the inventive method, the stored data include anesthesia data, narcosis monitoring data, and/or patient's vital signs. These elements can, for instance, be automatically captured by the relevant devices and made available by an OR network for storage. It is especially important to document such data, for instance for evaluation in the event of possible later complications.

In especially preferred manner, storage is activated depending on anesthetic data, narcosis monitoring data, and/or patient vital signs. These data indicate, among other things, when the narcosis is begun or ended. When, for instance, storage depends on the narcosis, it is possible in this manner to ensure that the storage begins at the point when the patient is under narcosis, while storage is not necessary when the patient is conscious. This can be an additional condition for activating storage, in addition to presence in the OR or a dependent condition, in particular when the area of injection or outlet of the narcosis is monitored, for instance by additional room cameras, and the relevant data are meant to be stored. Consequently this fulfills the need, for a patient under narcosis, that at least an indirect or subsequent visual control of procedures during the operation should be possible, whereas no storage is necessary during procedures that the patient can observe while conscious.

According to an additional configuration of the inventive method, the presence and/or identity of the patient and/or of other person is established by a wireless identification or tracking system. Such a system can be, for instance, a radio frequency identification device (RFID) system. As a result it becomes possible to make an identification with the help of RFID tags that are associated with the patient or other persons and, in particular, are carried on or in the body. It is also possible to obtain information wirelessly on the location of the relevant RFID tags, for instance by moving past an RFID reader device. In addition to wireless identification, it is possible to make identification by a wired or non-wireless system.

In an especially preferred manner, storage can occur in a ring memory, where it is possible for a user to have access to data and the data are then automatically erased and/or overwritten after a predetermined period if they are not called up. The ring memory can be configured as hardware or software, for instance on a server.

It is also possible to provide that a user can select whether there should be automatic erasing or overwriting after a predetermined period or whether this is controlled by the data, that is, when a predetermined memory space is used up. Dissolving or overwriting after a predetermined period has the advantage that a time frame can be indicated, based on the periods established for documentation or according to the period after which, for certain operations, no further complications usually arise. On the other hand, data-controlled erasing or overwriting has the advantage of maximum use of memory capacity.

An inventive device includes a data entry device for monitoring data from at least one data source. The data source here can be a video camera, for instance a room camera or an endoscopic video camera, as well as other data entry devices such as for instance a microphone for picking up sound data, as well as data capture by wirelessly readable data carriers such as RFID systems, or else a medical device or a monitoring device. These data can be captured by a data entry device, for instance by means of an interface that can also be integrated in the particular device, or a network that can ensure wired or wireless transmission. The data entry device can be configured for capturing data, for instance also from a data carrier such as a CD or DVD.

In addition the inventive device includes at least a storage device for storing data. This can, in particular, be a computer with a corresponding storage medium, for instance a hard disc, DVD, or other appropriate storage medium. In addition, it is possible to foresee at least one visual display unit to indicate data for a user and at least one entry device for entering data and/or instructions by the user. The display unit can, in particular, be a computer screen or other data output devices such as loudspeakers. For entering data and instructions, it is possible for instance to make available a keyboard, a touch screen, or a speech-activation device.

Because a storage device is provided that includes a first data storage configured as a ring memory on which the stored data in each case are erased after a predetermined time after they are entered, there is a guarantee that the storage medium is not exhausted but instead is always available for holding new data. It is also possible to ensure that the ring memory is configured for overwriting data if a predetermined memory capacity is exhausted.

If, for instance because of a complication following an operation, it becomes necessary to have access to the data recorded during this operation, then the respective relevant portion of the data can be removed from the ring memory and be stored in another memory for additional utilization, or else no additional data storage and thus no more data erasings occur on the ring memory, so that the data are available for evaluation. Thus an additional ring memory can be provided, which is then available for ongoing data storage.

According to a preferred embodiment, the storage device includes a second data memory, which is not configured as a ring memory on which data can likewise preferably be automatically stored. This has the advantage that some data, for instance those that require only limited storage space or which are intended for long-term storage, are not subject to regular erasing on the ring memory.

According to another embodiment, the user can control the entry of data into the first or the second data memory; that is, the user can indicate which data should be stored over the long term and which data can be erased after a certain period. This, like the establishment of the predetermined period, can be different for each user, so that in each case an identification or authorization of the user can be made necessary. Thus, depending on the type of data, for instance for various types of operations, an individually adjusted predetermination and thus an optimal use of storage place become possible.

According to an additional preferred embodiment, the entry of data into the first or second data memory can be influenced at least partially according to predetermined criteria that cannot be influenced by the user. Even the time after which the data stored in the ring memory are automatically erased can be predetermined regardless of the user. As a result, the fulfillment of quality assurance or legal requirements can be more securely established. An appropriate period after which the stored data can be erased if no access to them is made is, for instance, about four weeks, because as a rule any type of complications following surgery would have emerged within this time frame. Depending on the type of operation, even one week could suffice, or else a period of several months or even a year might be necessary.

According to an especially preferred embodiment, the stored data contains image information, in particular endoscopic image information, for instance endoscopic video images. Likewise the video images from a room camera, which takes in at least the area around the OR table, can be stored. The advantage here is that because of the storage of image data, an especially seamless documentation of the procedures in an operation becomes possible, for instance the subsequent recognition of errors or peculiarities that may have escaped the surgeon during the operation. Speech data can likewise be captured, for instance instructions entered into a speech control device, as well as other acoustic data such as speeches or noises from an OR. This too contributes to a particularly complete documentation of the procedures in an OR.

The inventive device can also, in particular, be configured for processing of stored data, in particular image data. The user thus has the means of adding comments, documents, research results, and the like to the image data, and of making comments in the image data, and so on.

In another especially preferred embodiment, the device is configured for entering and storage of data on the instruments and/or appliances used in a surgical operation. These data can includes, for instance, the type and serial or inventory numbers of the particular instruments or appliances. This makes possible a more complete documentation of all procedures during the operation. At the same time, likewise, data on the patient can be captured, in particular anamnesis data or else, for instance, vital signs during the operation.

According to an additional preferred embodiment, the data includes, in particular, information on the place and/or function and/or parameters of instruments and/or appliances used in the surgical operation. The data on functioning can, in particular, be the entered parameter such as, for instance, insufflation pressure or high voltage current, as well as measurements relating to them such as measured pressure, leaked current, temperature, and so on. In addition these can include the combined capture of anesthesia data and vital signs. This makes possible a particularly thorough documentation of the procedures in an operation.

According to another particularly preferred embodiment, the data are entered automatically. This can apply both to the entry of image data and to the entry of instrument and appliance data. This ensures thorough documentation, regardless of the situation in the operating room.

These data can be taken over, in particular, at least partially from a network, a computer system, and/or medical appliances, in particular an endoscopic video camera, or else for instance by a room camera. In particular in cases where the inventive device is configured for integration into a bus-controlled communication system inside the operation room, this is a simple and safe solution and one in which all other operational and safety-dependent requirements inside an operating room can be met. For instance, safety-relevant functions can be embedded in a closed system, whereas non-safety-relevant functions can be executed in an open system.

According to an additional preferred embodiment, the data are at least partially taken over by a wireless connection. Wireless connections of this kind are common in several areas; for instance, data inside and outside the OR can be transmitted by means of a WLAN. This has the advantage of dispensing with cable requirements that can hinder mobility.

According to another especially preferred embodiment, the device also includes at least one RFID identification and/or monitoring device. Thus, without further entry by the user, it is possible to determine automatically which instruments, sieves, appliances, and the like equipped with a corresponding code carrier were used in an operation, and in some cases even in what configuration and at what time.

According to another preferred embodiment, the storage of data in the ring memory is triggered by the presence of a patient in the operating room. This makes it possible to prevent non-relevant data, such as video images or speech data from a non-used OR, from unnecessarily taking up memory capacity. On the other hand, this makes it possible to ensure reliably that whenever the data could be relevant, they are also stored, for instance for quality assurance. The patient's presence could be determined, for instance, by image processing methods.

It is especially preferable, however, if the presence of the patient can be detected by a wireless information system, for instance an RFID system. Advantageously, it is also possible simultaneously to make an identification of the patient or else of the transmission of patient-specific data. Thus the patient data can be made available for purposes of documentation as well as intraoperatively and immediately to the surgeon. For this purpose the patient in particular or the transport vehicle of the patient, for instance, can bear an RFID code label or other means of identification.

According to an additional preferred embodiment, accordingly, the storage of data in the ring memory is automatically terminated when the patient leaves the OR. This also ensures that memory capacity is not taken up unnecessarily.

An inventive system for executing medical interventions includes a device for control and/or monitoring of at least one apparatus, at least one apparatus that is for use in a medical intervention and is connected with the control and/or monitoring device, and one device for documentation of medical data according to any one of the aforementioned claims. Such a total system supports in simple and safe manner the execution and automatic documentation of all procedures during an operation.

In this case the data necessary for complete documentation can be captured and stored in particular in cases where the system also includes means for identifying and/or localizing medical instruments, medical appliances, and or persons. Such means can be, in particular, an RFID system.

For detecting whether a patient is being brought into the OR or is leaving the OR, it can be advantageous to install an RFID reader device in the entry area of the OR or else several successive gates in the direction traveled, each having an RFID reading device, for instance at the entry door of the OR. In this way, likewise, it is possible to recognize the direction of motion by means of instruments, sieves, appliances, personnel, and so on equipped with RFID code labels. This makes it possible, independently of the detection inside the OR, to determine which persons and/or objects are located in the OR at a particular time.

In the event that, in passing through the gates, a correct detection should occur only in one of the two gates, an arrangement can be made whereby the motion direction is automatically ascertained or manually entered by an additional input instrument. Thus for instance a warning signal such as a warning tone can be emitted. The relevant person whose motion direction has not been detected can then enter the motion direction, for instance by means of an input button positioned close to the gate. The same is true if the patient's motion direction has not been unequivocally recognized. This has the advantage that no additional passage through both gates is required for recognition of the present in the OR.

In addition, a personal identification system can be provided whereby the additional persons present in the OR can be unequivocally identified. A secure identification in this case is made in particular by biometric recognition data. Once established, the identification likewise is preferably stored. In a particularly advantageous manner the identification is made through non-touch input systems, for instance iris biometry or facial measurement followed by automatic image processing.

It is understood that the aforementioned characteristics, as well as those characteristics yet to be disclosed, can be applied not only in the individually indicated combination but also in other combinations or individually, without departing from the framework of the present invention.

Further aspects of the invention can be seen in the following description of preferred embodiments and the appended illustration.

BRIEF DESCRIPTION OF THE DRAWINGS

FIG. 1a shows preferred embodiments of an inventive device in schematic form;

FIG. 1b shows a schematic diagram of another embodiment of the present invention; and FIG. 1c shows a schematic of an embodiment of the present invention with sensor and RFID label.

DETAILED DESCRIPTION OF THE INVENTION

According to FIG. 1a, a control computer 10 serves as input device for entering instructions by the user and for displaying captured or stored data, in particular image data. The control computer 10 is connected with a network 30 by a network connection 30". Data can be exchanged by the network 30. An endoscopic video camera 35, which serves to capture image data obtained by an endoscope, is connected with the network 30 by an additional network connection 30". The endoscopic video camera 35 is connected to a ring memory 20 by the connecting line 30', which makes possible the exchange of data. Through additional connections 30", additional medical appliances 40 can be connected to the network 30. They can consist of appliances in any quantity such as pumps, high voltage generators, insufflation devices, suction devices, respiratory devices, and so on. They can transmit the values of operating parameters by means of the network 30, for instance. In addition the appliances can be powered or supplied with current by the network 30, for instance.

FIG. 1b shows a second preferred embodiment of the inventive device. Here the ring memory 20 is connected connecting line 30' with an entry device 10' in the form of a personal computer. The personal computer 10' is connected with the control device 10 of the network 30 by a data line 31. Data, captured for instance by the video camera 35, are transmitted by the network 30 to the control device 10, which in turn makes possible a transmission of the data onto the personal computer 10' through the data line 31. In addition to the ring memory 20, the documentation device 1 in FIG. 1b has at its disposal additional memory capacity, which is located in each case in the control units 10' and 10 and can be applied, for instance, according to the particular requirements.

According to FIG. 1c, in addition a reception station 60 can be provided which is connected with the network 30 by a network connection 30". A sensor 80, for instance a radio signal receiver, is positioned on the reception station 60. The sensor 80 receives the signals, which a transponder, for instance in the form of an RFID label 70 affixed on a surgical instrument or on a patient, emits. This signal can serve, for instance, to start the storage of the data transmitted by the network 30 in the ring memory 20 by means of the network 30.

The remaining portion of the inventive device according to the embodiment in FIG. 1c can also be configured in especially preferred manner as seen in FIG. 1b.

According to an embodiment of the present invention, the patient, who is normally not fully conscious while in the OR, wirelessly actives the security monitoring or data documentation in the operating room by wearing an identification element on or in the body. Activation occurs, for instance, by means of an RFID gate system at the entrance to the OR. The patient here wears an RFID identification element on or in the body. Storage of data in the ring memory can occur through a linking of the signal of the RFID identification element with the vital signs of the narcosis monitoring; that is, storage is activated when the patient is in the OR and under narcosis. This recognizes the patient's desire that, even when unconscious, he or she can activate a certain indirect audio-visual control.

The RFID identification and/or tracking device consists of one or more identification elements that the patient and/or surgery staff wear, and RFID reception units, which securely capture information or identification elements via touch-less means. Ideally, a type of gate consists of several RFID reception units that are installed spatially in a row, so that it is possible to decide unequivocally whether the patient is entering the OR at the moment, that is, is received in the gate, or instead is leaving the OR. When the patient enters the OR, the security monitoring and data storage are started; when the patient leaves the OR, then recording in the ring puffer is stopped.

The storage device can be coupled to a personal identification system with which all members of the OR team unequivocally identify themselves before the start of the operation by biometric markers filed in the system with respect to the patient and his or her impending operation. Because of the sterile situation, this occurs touchlessly with special video camera-supported entry systems, such as Iris biometry and/or facial measurement. This identification of the OR team with respect to the present patient and the impending operation is also documented and stored.

The invention claimed is:

1. A method for documentation of medical data with a documentation system comprising:
   receiving with the documentation system data from an operating room, the data captured by at least one data entry device and including video data from a video camera;
   automatically activating with the documentation system a storage medium, the activating only in response to sensing with a sensor entry of a patient to be operated upon into said operating room, the sensing including sensing with the sensor an identifier associated with the patient;
   storing with the documentation system said data in said storage medium only after said storage medium is activated.

2. The method of claim 1, wherein said storage medium is activated only in the presence of an additional person in said operating room.

3. The method of claim 1, wherein said data are taken from a group comprising a network, a computer system, or a medical device or a combination thereof.

4. The method of claim 3, wherein said medical device is an endoscopic video camera generating video data, the storage medium storing the video data after said storage medium is activated.

5. The method of claim 1, wherein said data include information selected from a group comprising image information or speech data, or a combination thereof.

6. The method of claim 5, wherein image information is endoscopic image formation.

7. The method of claim 1, wherein said data include information selected from a group comprising type, location, function, parameters of surgical instruments or appliances, or a combination of information thereof.

8. The method of claim 1, wherein said data is selected from a group comprising anesthesia data, narcosis monitoring data, or vital signs of a patient, or a combination thereof.

9. The method of claim 8, wherein said storage is activated depending on said data of said patient.

10. The method of claim 1, wherein the presence or identity of said at least one person is established by a wireless identification or tracking system.

11. The method of claim 1, wherein said storage medium occurs in a ring memory, and where access to said data is possible for a user and where erasing or overwriting of said data occurs after a predetermined time if no accessing has occurred.

12. The method of claim 1, further comprising deactivating the storage medium when the patient leaves said operating room.

13. The method of claim 1, wherein entry of the patient into said operating room is determined with an RFID system and a plurality of gates installed at one or more entry regions of the operating room, each with an RFID reader, that identify movement of the patient equipped with an RFID code.

14. A device for documenting medical data comprising:
   at least one data reception device for receiving data from at least one data source,
   at least one storage device for storing said data,
   said at least one storage device configured to be activated only in response to sensing with a sensor entry of a patient to be operated upon into said operating room;
   at least one visual display unit for viewing said data, and
   at least one entry device for entering said data or instructions, wherein said storage device contains a first data memory configured for automatic erasing or overwriting said data after a predetermined time.

15. The device of claim 14, wherein said storage device contains a second data memory which is not configured for automatic erasing or overwriting of data after a predetermined time.

16. The device of claim 14, wherein said device further includes at least one RFID identification or tracking device in the entrance area of an operating room.

17. The device of claim 16, wherein at least one means is provided for identifying or tracking selected from a group consisting of medical instruments, medical appliances, or persons, or a combination thereof.

18. The device of claim 14, wherein it is configured for executing a method involving the steps of introducing data from an operating room, captured by at least one data entry device, and storing said data in a storage medium, said storage medium activated by the presence of at least one person in said operating room.

19. The device of claim 18, wherein said at least one person is to be operated upon.

20. A system for conducting medical interventions, comprising:
   a device for controlling or monitoring at least one apparatus;
   said device connected to said at least one apparatus;
   said at least one apparatus for use in a medical intervention and including an endoscopic video camera generating video data;
   a second device connected with said control or monitoring device for documenting medical data;
   said second device comprising a storage device having computer instructions executing on computer readable media configured to activate the storage device only in response to sensing with a sensor entry of a patient to be operated upon into said operating room, the entry of the patient determined with an RFID system and a plurality of gates installed in an entry region of the operating room;

said storage device storing the video data upon activation and comprising a ring memory such that the video data stored on the storage device is deleted or overwritten after a predetermined period of time.

* * * * *